United States Patent [19]
Zofchak et al.

[11] Patent Number: 6,107,352
[45] Date of Patent: Aug. 22, 2000

[54] POLYMERIC DIFUNCTIONAL CATIONIC EMOLLIENTS AND CONDITIONERS FOR USE IN COSMETIC, PERSONAL CARE AND HOUSEHOLD PRODUCTS

[75] Inventors: Albert Zofchak, Matawan; Madeline Kenney, Caldwell; John Obeji, Clifton; Michael Mosquera, Forked River, all of N.J.

[73] Assignee: Alzo, Inc., Sayreville, N.J.

[21] Appl. No.: 09/062,860

[22] Filed: Apr. 20, 1998

[51] Int. Cl.$^7$ ............... A61K 7/06; A61K 7/11; A61K 7/15; A61K 7/00
[52] U.S. Cl. ............ 516/914; 516/917; 424/70.11; 424/70.17; 424/73; 424/401; 514/873
[58] Field of Search ................ 424/401, 70.11, 424/70.12, 73; 252/351, 356, 357; 514/873; 516/914, 917

[56] References Cited

U.S. PATENT DOCUMENTS

| | | |
|---|---|---|
| 4,537,762 | 8/1985 | Fogel et al. ............... 424/70 |
| 4,548,810 | 10/1985 | Zofchak . |
| 4,940,573 | 7/1990 | Sebag et al. . |
| 5,674,479 | 10/1997 | George et al. . |

Primary Examiner—Shelley A. Dodson
Assistant Examiner—Marina Lamm
Attorney, Agent, or Firm—Henry D. Coleman; R. Neil Sudol

[57] ABSTRACT

The present invention also relates to chemical compositions comprising the neutralization product of at least one amine neutralization compound (preferably, a diamine) and a carboxylic acid (preferably, a dicarboxylic acid), said amine neutralization compound comprising about 1% to about 100% by weight (of the total amount of amine neutralization containing compound) of a first amine compound and 0% to about 99% by weight of a second amine compound different from said first amine compound, said first amine compound being a polyamine containing at least one tertiary amine group and at least one quaternary amine group, said tertiary amine group of said first amine reacting with said carboxylic acid group to produce a tertiary ammonium carboxylate salt, said second amine compound containing at least one primary, secondary or tertiary amine group with the proviso that when said second amine contains only primary and/or secondary amine groups, the amount of said second amine in said amine neutralization compound is no greater than about 20% (preferably, no greater than about 10%) by weight and said carboxylic acid comprises at least about 50% by weight (more preferably at least about 75% by weight, even more preferably about 90% by weight and even more preferably about 100% by weight of a polycarboxylic acid, more preferably a dicarboxylic acid.

39 Claims, 3 Drawing Sheets

FIGURE 1

NEQUAT DAS-D

R = Propyl
D = Dimer Dilinoleate

Chemical Name: Bis [Dimer Dilinoleate - Bis - (Amidopropyl - N,N-Dimethyl Ammonium Ethyl Sulfate)
Dimer Dilinoleate Quat / Ammonium Salt.

FIGURE 2

NEQUAT DS-D (SO-D)

R = Propyl
R1 = Soya (C18H35)
D = Dimer Dilinoleate

Chemical Name: [Dimer Dilinoleate Bis-(Amidopropyl-N,N-Dimethyl) Ammonium Ethyl Sulfate / Soyamidopropyl-N,N-Dimethyl] Dimer Dilinoleate Quat / Ammonium Salt.

FIGURE 3

NEQUAT DL-D

R = PROPYL
R1 = Linoleyl
D = Dimer Dilinoleate

Chemical Name: [Dimer Dilinoleate-Bis-(Amidopropyl-N,N-Dimethyl) Ammonium Ethyl sulfate /Linoleamidopropyl-N,N-Dimethyl Dimer Dilinoleate Qunt/ Ammonium Salt

POLYMERIC DIFUNCTIONAL CATIONIC EMOLLIENTS AND CONDITIONERS FOR USE IN COSMETIC, PERSONAL CARE AND HOUSEHOLD PRODUCTS

FIELD OF THE INVENTION

The present invention relates to novel polymeric ionic compounds which can be used as emollients and conditioners in cosmetic, personal care and household products.

BACKGROUND OF THE INVENTION

Quaternaries of long chain fatty amines have been used for many years primarily in hair contacting formulations for their antistatic properties, as well as the favorable wetting and conditioning characteristics. In addition, these compounds promote dry combing and assist in detangling when used in hair care formulations in conjunction with long chain tertiary amine oxides. Various tertiary amine quaternaries are considered to be irritants which limit their use in skin and hair contacting formulations.

Tertiary amines of $C_{12}$ to $C_{18}$ chain lengths which are quaternized with aromatic intermediates such as benzyl chloride, methylbenzyl chloride, and dibenzyl chloride have been used for many years in hair contacting formulations to promote conditioning, ease of wet and dry combing and reducing or preventing flyaway hair. In addition, benzyl chloride quaternaries have also been used as bacteriastats and fungicides and are used in hard surface cleaners as sanitizing agents and in swimming pools as algacides.

Quaternaries such as dimethyl dihydrogenated tallow amine chlorides have long been used as low cost fabric softeners at concentrations ranging from about 4% to about 8% on a total weight basis. Quaternaries such as trimethyl cetyl ammonium chloride have been used as standards for exceptional conditioning and management of hair in cosmetic and personal care products. Quaternaries derived from cocodimethyl amine and lauryl dimethyl amine have been used as the basis for "hot" wax applications for car washes. Diethyl sulfate quaternaries derived from $C_{12}$ to $C_{18}$ as well as ethoxylated teriary amines have been long used in the textile industry as lubricants and softening agents.

Long chain tertiary amine salts of fatty acids ranging from $C_6$ through $C_{36}$ have been used successfully on a commercial basis and sold under the tradename NECON. These tertiary amine salts have been used in skin and hair contacting formulations in such applications as shaving creams, skin creams, lotions, bar soaps, liquid soaps, body oils, hair colorants, afterbath lotions and splashes, lipsticks, lip balms, bath products and sunscreen formulations for their attributes of assisting in the solubilization of components in these formulations, their conditioning characteristics and their promotion of adherence to the skin and hair.

Physical blends of long chain tertiary amine salts and tertiary amine quaternaries which have been quaternized with dimethyl sulfate, diethyl sulfate, methyl chloride and benzyl chloride, among others have been effective as compounds having characteristics of instilling favorable characteristics in hair care products.

SUMMARY OF THE INVENTION

Compositions of the present invention relate to molecular structures which contain moieties of varying chain lengths having varying degrees and types of tertiary amine quaternization. Compositions according to the present invention provide unique features in end-use applications in cosmetic, toiletry and personal care products as well as in household products, for example, hard surface and textile/carpet cleaners as well as anti-static products.

In one aspect, the present invention relates to novel compositions of the structure:

where Y is a dicarboxylate derived from an organic dicarboxylic acid and $X_1$ is a polyamine, preferably a diamine, said polyamine comprising at least one tertiary amine group and at least one quaternary amine group and wherein $X_2$ is an amine, preferably a polyamine containing at least one tertiary amine group (preferably, a diamine containing two tertiary amine groups or a tertiary amine group and a quaternary amine group) and wherein $X_2$ is the same or different than $X_1$.

In preferred aspects according to the present invention, Y is a dicarboxylate derived from a $C_2$–$C_{50}$ dicarboxylic acid, preferably a $C_5$–$C_{37}$ dicarboxylic acid, even more preferably the dicarboxylic acid is dimer dilinoleic acid and $X_1$ is preferably a diamine containing a tertiary amine and a quaternary amine and at least one amide group within its structure.

The present invention also relates to chemical compositions comprising the neutralization product of at least one amine neutralization compound (preferably, a diamine) and a carboxylic acid (preferably, a dicarboxylic acid), said amine neutralization compound comprising about 1% to about 100% by weight (of the total amount of amine neutralization containing compound) of a first amine compound and 0% to about 99% by weight of a second amine compound different from said first amine compound, said first amine compound being a polyamine containing at least one tertiary amine group and at least one quaternary amine group, said tertiary amine group of said first amine reacting with said carboxylic acid group to produce a tertiary ammonium carboxylate salt, said second amine compound containing at least one primary, secondary or tertiary amine group with the proviso that when said second amine contains only primary and/or secondary amine groups, the amount of said second amine in said amine neutralization compound is no greater than about 20% (preferably, no greater than about 10%) by weight and said carboxylic acid comprises at least about 50% by weight (more preferably at least about 75% by weight, even more preferably about 90% by weight and even more preferably about 100% by weight of a polycarboxylic acid, more preferably a dicarboxylic acid. In preferred aspects according to the present invention, the polycarboxylic acid is a dicarboxylic acid, the first amine is a diamine containing a tertiary amine group and a quaterary amine group and the second amine is a diamine containing only tertiary amine groups or tertiary amine groups and quaternary amine groups. The molar ratio of the amine neutralization compound and the polycarboxylic acid may preferably range from about 1:10 to about 10:1 (depending upon the number of amine groups and carboxylic acid groups within the amine neutralization compound and the polycarboxylic acid respectively), more preferably about 1:3 to about 3:1 and even more preferably about 1:1, it is clearly preferred that the molar ratio of the amine neutralization compound to the polycarboxylic acid be chosen so that all of the primary, secondary or tertiary amine groups have been substantially (i.e., less than 5% of the original molar concentration of free amine groups or carboxylic acid groups remains) or completely exhausted (less than about 0.5% and more preferably less than about 0.1% by weight of free amine or carboxylic acid groups remain.

In preferred aspects according to the present invention, the polyamine of the amine neutralization compound contains at least one amide group (in addition to the amine groups) and is preferably derived from fatty acids or esters such as triglycerides including those contained in safflower seed oil and methyl and ethyl esters of fatty acids, among numerous others. In the present invention, the quaternary group (i.e., that group which is covalently bonded to the tertiary amine group in forming the quaternary amine group) may be any group which is compatibile with the formation of quaternary amine groups for use in the present invention and is preferably a methyl, ethyl or benzyl group; and the polycarboxylic acid is preferably a dicarboxylic acid. In more preferred aspects of the present invention, the tertiary amine is a fatty amido tertiary amine and the carboxylic acid is a dicarboxylic acid.

Emulsion based formulations for inclusion in cosmetic, personal care and cleaning compositions (e.g., detergents, textile cleaners, hard surface cleaners and carpet cleaners) of the present invention comprise about 0.05% to about 95% by weight of the compositions according to the present invention, the remainder of the emulsion formulation comprising any one or more of water, emulsifiers, surfactants, preservatives, colors, humectants, secondary moisturizers, secondary conditioners, emollients, lubricity additives, softeners, bioactive agents (anti-dandruff agents, insect repellents, etc.), fragrances, among numerous others including thickeners represent another aspect of the present invention.

Methods of using the present compositions for enhancing certain advantageous characteristics and/or reducing certain disadvantageous characteristics of end-use cosmetic, personal care or household formulations such as hair care formulations including shampoos, conditioners, hair rinses, hair colorants, permanent wave formulations and hair straighteners, skin lotions and creams, shaving creams, gels and lotions, sunscreens, deodorants and anti-perspirants, bar and liquid soaps, detergents and fabric softeners, hard surface and textile (including carpet) cleaners represents another aspect of the present invention. The present method may be used to enhance such characteristics including conditioning, viscosity, lubricity, detangling, comb facilitation (wet and dry combing) and wettability or to reduce static electricity, irritation (especially, for example, in shave creams, gels and other formulations), among numerous other characteristics are also contemplated by the present invention. These methods comprise including in end-use compositions an amount of the present compositions effective for producing the desired result.

Compositions according to the present invention preferably build into a molecule or composition varying carbon chain length, tertiary amine quaternization and tertiary amine salts (based upon the neutralized carboxylic acid to form tertiary ammonium carboxylate salts) which may favorably impact a number of physical and chemical characteristics of the compositions. The variety of characteristics which may be built into the compositions according to the present invention and the flexibility with which compositions according to the present invention exhibit when utilized in personal care, cosmetic, toiletry and household formulations represents an advance in the state of the art.

The wide range in variability of the chemistry of the present invention makes it possible to provide favorable characteristics for a wide range of commercial products. The present invention provides those of ordinary skill with the ability to "design" a chemical compound to enhance or achieve a selected characteristic desirable in final formulations according to the present invention.

It is possible to build or design and vary composition size by varying individual components of the present invention, for example, the tertiary amine salts, the degree and type of quaternization utilized, the type and amount of carboxylic acid utilized. Consequently, the present invention finds use in the following areas of application, among numerous others:

as conditioners to promote the softening of hair and skin;

as sheening agents to provide gloss and body to hair;

as emollients for use in creams and lotions for the skin;

as lubricity additives for use in shave cream formulations;

as conditioning additives for shampoos with excellent compatibility with anionic surfactants;

as emulsifying agents for creams and lotions either alone or in combination with other emulsifying agents;

as slip emulsifying agents for creams and lotions;

as agents to enhance the substantivity of sunscreens in sunscreen formulations;

as agents to prevent static electricity in hair and household products;

as detangling additives for hair formulations;

as agents to provide sheen to hair and skin in hair and skin products;

as facilitators for wet and dry combing;

as lubricants and conditioners in pre-electric shave lotions/formulations;

as conditioners in after shave lotions;

as conditioners in hair straighteners and permanent wave formulations;

as viscosity building agents in hard surface and carpet cleaners;

as conditioners and softening agents in soap bars;

as conditioners in hair colorant formulations.

Preferred tertiary amines for use in the present invention have the following general formula I:

where R' is a $C_6$ through $C_{36}$ linear or branch-chained saturated or unsaturated alkyl group which is substituted or unsubstituted, monomeric or dimeric, a phenyl or benzyl group or substituted phenyl or benzyl group, an alkylphenyl, alkylbenzyl or substituted alkylphenyl or alkylbenzyl group; and R", $R_1$ and $R_2$ are selected from a $C_1$ through $C_{36}$ linear or branch-chained saturated or unsaturated alkyl group which is substituted or unsubstituted, monomeric or dimeric, a phenyl or benzyl group or substituted phenyl or benzyl group, an alkylphenyl, alkylbenzyl or substituted alkylphenyl or alkylbenzyl group, or poly(alkylene oxide) ranging in size from about 2 to about 150 alkylene oxide units. Preferably, $R_1$ and $R_2$ are $C_1$ through $C_{15}$ linear or branch-chained alkyl groups, more preferably, methyl, ethyl, propyl or isopropyl groups. As used in the present invention, these preferred tertiary amines may be used without further modification to neutralize the polycarboxylic acid (essentially as $X_2$), or further quaternized (essentially as $X_1$).

Substituents may include for example, halogens such as fluorine, chlorine and bromine, nitro groups, amine groups, substituted amine groups, hydroxyl groups, alkoxy groups, substituted alkoxy groups, substituted alkoxy groups, alkyl groups or substituted alkyl groups, among numerous others. One of ordinary skill in the art will be able to recognize modifications which readily may be made to the present compositions to instill desirable characteristics in the present compositions.

In preferred aspects, tertiary amines according to the present invention are quaternized with a quaternizing agent or neutralized with a carboxylic acid to produce compositions according to the present invention. The preferred carboxylic acids are dicarboxylic acids.

DETAILED DESCRIPTION OF THE INVENTION

The following terms shall be used throughout the specification to describe the present invention:

The term "tertiary amine" is used to describe an amine to which is attached at least three carbon-containing groups, each of the groups being covalently bonded to the amine group through a carbon atom within the group. Exemplary tertiary amines, include for example, trialkyl amines of the general formula:

where one or more of R', R" and R'" is a carbon-containing group selected from a straight or branch-chained, saturated or unsaturated $C_1$ to $C_{30}$ alkyl or substituted alkyl group, phenyl, substituted phenyl, benzyl, substituted benzyl, or poly(alkylene oxide) ranging in size from about 2 to about 150 units, Preferred tertiary amines for use in the present invention include those of the following structure, which may be separately referred to as amidoamines or amido tertiary amine:

where R' is a $C_6$ through $C_{36}$ linear or branch-chained saturated or unsaturated alkyl group which is substituted or unsubstituted, monomeric or dimeric, a phenyl or benzyl group or substituted phenyl or benzyl group, an alkylphenyl, alkylbenzyl or substituted alkylphenyl or alkylbenzyl group, or poly(alkylene oxide) ranging in size from about 2 to about 150 moles; R", $R_1$ and $R_2$ are selected from a $C_1$ through $C_{36}$ linear or branch-chained saturated or unsaturated alkyl group which is substituted or unsubstituted, monomeric or dimeric, a phenyl or benzyl group or substituted phenyl or benzyl group, an alkylphenyl, alkylbenzyl or substituted alkylphenyl or alkylbenzyl group, or poly(alkylene oxide, preferably ethylene oxide or ethylene oxide-co-propylene oxide) ranging in size from about 2 to about 150 alkylene oxide units.

Exemplary tertiary amines for use in the present invention include, for example, polyoxyethylcocoamine (ranging from 2 to 150 units of ethylene oxide), polyoxypropyl cocamine (ranging from 2 to 150 units of propylene oxide), polyoxyethyl soyamine (ranging from 2 to 150 units of ethylene oxide), polyoxypropyl soyamine (ranging from 2 to 150 units of propylene oxide), polyoxyethylene tallow amine (ranging from 2 to 150 units of ethylene oxide), polyoxypropyl tallow amine (ranging from 2 to 150 units of propylene oxide), polyoxyalkylene oxide of caprylic amine (ranging from 2 to 150 units of alkylene oxide), polyoxyalkylene oxide of capric amine (ranging from 2 to 150 units of alkylene oxide), polyoxyalkylene oxide of lauryl amine (ranging from 2 to 150 units of alkylene oxide), polyoxyalkylene oxide of myristyl amine (ranging from 2 to 150 units of alkylene oxide), polyoxyalkylene oxide of palmityl amine (ranging from 2 to 150 units of alkylene oxide), polyoxyalkylene oxide of stearyl amine (ranging from 2 to 150 units of alkylene oxide), polyoxyalkylene oxide of erusyl amine (ranging from 2 to 150 units of alkylene oxide), polyoxyalkylene oxide of behenyl amine (ranging from 2 to 150 units of alkylene oxide), 3-diethylaminoproyl amine, diethylisopropanolamine, diisopropanolamine, dimethylethanolamine, dimethylisopropanolamine, diethyl palmitylamine, diethylstearyl amine, N-(2-Hydroxyethyl) piperazine, N-isopropyldiisopropanolamine, N-methyl morpholine, alpha-methylbenzyl diethanolamine, methylphenylethanolamine, phenyldiethanolamine, triisopropanolamine, dihydrogenated tallow methyl amine, dicocomethyl amine, dibehenyl methyl amine, among numerous others, including amidified tertiary amines such as those formed from transamidation of C6 to C30 or higher carbon fatty acids derived from synthetic or natural product trigycerides including coconut oil, soybean oil, sunflower oil and tallow, and polyamines (i.e., those compounds containing at least two amine groups, at least one of which is a tertiary amine) such as dimethylaminopropyl amine. Examples of these amidified tertiary amines include, for example, cocoamidopropyldimethyl amine, linoleylamidopropyldimethyl amine and ricinoleyl amidpropyldimethyl amine, among others including amidified tertiary amines derived from trimeric or polymeric tertiary amines (for example, as derived from polycarboxylic acids. Most preferably, the tertiary amines used in the present invention include linoleamidopropyl dimethyl amine, linoleamidopropyl dimethylamine and related tertiary amines.

The term "alkylene oxide" refers to a polymeric group of repeating units of the general formula $(R_7-O)_n$ — where $R_7$ is a $C_2$ to $C_8$ alkyl group, preferably a $C_2$ to $C_6$ alkyl group, preferably a $C_2$ to $C_4$ unbranched alkyl group, most preferably a $C_2$ to $C_3$ unbranched alkyl group and n ranges from 2 to 150 units (corresponding to 2 to 150 moles of alkylene oxide) within that group.

The term "carboxylic acid" as used herein describes organic acids which may contain one or more carboxylic acid moieties preferably ranging in size from $C_2$ to $C_{50}$ or more. The term "monocarboxylic acid" is used to describe organic acids which contain only one carboxylic acid moiety. Monocarboxylic acids are used in the present invention, if at all, in minor amounts, generally less than about 20% by weight of the total amount of carboxylic acid used in the present invention, more preferably less than about 10% by weight. The term "polycarboxylic acid" is used to describe organic acids which contain at least two carboxylic acid moieties. Those polycarboxylic acids which contain only two carboxylic acid moieties may also be referred to in this specification as "dicarboxylic acids".

Exemplary carboxylic acids for use in the present invention include, for example, pentanoic acid, neopentanoic acid, caproic acid, caprylic acid, capric acid, heptanoic acid, neoheptanoic acid, octanoic acid, iso-octanoic acid, 2-etlhylhexanoic acid, nonanoic acid, isononanooic acid, decanoic acid, iso-decanoic acid, neodecanoic acid, undenanoic acid, undecylenic acid, lauric acid, isolauric acid, myristic acid, palmitic acid, stearic acid, hydroxy stearic acid, isostearic acid, arachidonic acid, tallow fatty acid, arachidic acid, behenic acid, lignoceric acid, lauroleic acid, myristoleic acid, palmitoleic acid, olelic acid, gadoleic acid, erusic acid, ricinoleic acid, linolenic acid, linoleic acid, lactic acid, glycolic acid, mandelic acid, eicosopentaoic acid, phenylstearic acid, retinoic acid, salicylic acid and benzoic acid, among numerous others, including dimer acids, trimer acids, adipic acid, azealeic acid, malic acid, succinic acid, dodecandioic acid, citric acid, tartaric acid, sebacic acid, fumaric acid, glucaric acid, glutaric acid and oxalic acid, among others.

Preferred polycarboxylic acids for use in the present invention include, for example, $C_2$–$C_{50}$ dicarboxylic acids, including dimer, trimer and tetramer acids which are made from the dimerization, trimerization or tetramerization of long-chain unsaturated acids, such as linoleic acid, among numerous other acids, including mixtures of these acids, more preferably including $C_5$–$C_{37}$ dicarboxylic acids and mixtures of these acids. Dilinoleic acid is a preferred dicarboxylic acid. Other acids which may be preferably used in the present invention include, for example, adipic acid, azealeic acid, malic acid, succinic acid, dodecandioic acid, citric acid, tartaric acid, sebacic acid, fumaric acid, glucaric acid, glutaric acid and oxalic acid, among others. Preferred dicarboxylic acids containg carboxylic groups at the terminal ends of the molecule.

Other exemplary polycarboxylic acids include, for example, polymeric products containing carboxylic (carboxylate) side chains, such as acrylic or (meth)acrylic, polyesters, cellulosic polymers, polyvinyl alcohol, polysiloxanes, oligo and polypeptides, among numerous others.

The term "quaternizing agent" is used throughout the specification to describe compounds which are used to react with tertiary amines to produce quarternary salts according to the present invention. Quaternary salts are salts which are produced when a tertiary amine is reacted with a quaternizing agent to produce an amine which is substituted with four carbon-containing groups. The quaternary amine produced is cationic and is generally found complexed with an anionic group or "counterion", which is generally derived from the quaternizing agent used to produce the quaternary amine. Exemplary quaternizing agents for use in the present invention include, for example, dimethyl sulfate, diethyl sulfate, methyl bromide, benzyl chloride, ethyl benzyl chloride, methyl benzyl chloride, dichloroethyl ether, epichlorohydrin, ethylene chlorohydrin, methyl chloride, pyridinium chloride and allyl chloride, among others, such that the group reactive with the amine produces an group with the amine and the positively charged quaternary aminegroup is complexed with an anionic group or counterion, which is represented as $T^-$. The counterion may be any group which is anionic and is compatible with the chemistry of the present invention and preferably is an anionic chloride, bromide, iodide, fluoride, sulfate (mono- or di-anion, preferably alkyl substituted mono-anion such as methyl or ethyl sulfate, more preferably ethyl sulfate) and phosphate (mono-, di- and tri-anion, preferably tri-anion), among numerous others, with anionic chloride and sulfate (alkyl substituted mono-anion) being the preferred counterion $T^-$.

The compositions according to the present invention may be varied in one or more of the following ways:

1. Increasing or decreasing the degree of quaternization within the range of about 1% to about 99% by weight of the starting tertiary amine within the composition—such variation will affect the following characteristics of the final compositions: detangling, conditioning, antistatic and substantivity properties of the moiety as well as the solubility of the final composition.

2. Increasing or decreasing the ratio and componentry of the tertiary amine used in the final composition. For example, by increasing or decreasing the ratios of fatty amines to bis-tertiary amines. Such variations will affect the degree of conditioning (for hair, skin or fabric) as well as impact wet and dry combing characteristics of final formulations utilizing the present compositions, sheen and lustre properties of the hair on which the compositions according to the present invention are used.

3. Increasing or decreasing saturation/unsaturation in the side chains of the tertiary amines or dicarboxylic acids used in the present compositions. Increased unsaturation will generally result in enhanced lubricity and softening of hair, skin and fabric.

4. Increasing or decreasing the degree of neutralization. Such variations will affect the viscosity and thickening properties of the present compositions and final formulations which utilize these compositions as well as their solubility and conditioning properties for formulations to be used in hair and skin formulations as well as formulations to be used to treat fabrics.

5. Increasing or decreasing the chain length of the monofunctional or difunctional carboxylic acid. Such variations will affect the viscosity and bodying properties as well as the solubility, stability and conditioning properties of the present compositions. The use of dimer acid salts will instill outstanding conditioning and thickening properties to the present compositions and provide enhanced stability to pH extremes as well as reduced irritation associated with use of the present compositions compared to conventional quaternaries.

5. Increasing or decreasing the chain length of the tertiary fatty amine, either alone or in combination with other tertiary amines (amine blend). Such a variation will affect the degree of conditioning for formulations to be used on hair, skin and fabrics, impact the wet and dry combining characteristics of final formulations as well as the sheen and lustre which are instilled. Increased unsaturation in the fatty amines will result in enhanced lubricity and softening of hair and fabric.

The above-described examples provide insight into the unlimited number of possible variations in the present invention which can be developed to provide highly desirable and novel properties and characteristics which exceed those of traditional additives used as conditioners in personal care and household products. One of ordinary skill relying on information set forth in this specification as well as that which is generally known will be able to readily modify the compositions according to the present invention in order to instill desired characteristics in the present compositions as well as formulations which include compositions according to the present invention.

It has been discovered unexpectedly that compounds of the present invention are excellent conditioners in personal care products and exhibit favorable properties in the following systems:

shave creams;
women's toiletries for shaving preparations;
depilatories;
relaxers;
permanent wave formulations;
2-in 1 shampoos
hair colorants Compounds according to the present invention preferably are derived from fatty diamido amines, preferably amido tertiary amines such as dilinoleamidopropyl dimethyl amine or linoleamidopropyl dimethyl amine, although numerous other fatty amido tertiary amines may also be used in the present invention. Most preferably, compounds according to the present invention include, for example, linoleamidopropyl ethyl dimonium ethosulfate dimer dilinoleate or dilenoleamidopropyl dimethyl amine dilinoleate and related compounds, where the fatty amido tertiary amine has been quaternized with ethyl sulfate and subsequently acidified with dimer dilinoleic acid.

In general, compositions according to the present invention are included in end-use formulations in amounts ranging from about 0.025% to about 50% by weight, more preferably about 0.50% to about 20% by weight, depending upon the end-use.

For example, in shampoos, rinses, conditioners, hair straighteners, hair colorants and permanent wave formulations, the compositions according to the present invention preferably comprise about 0.25% to about 20% by weight, more preferably about 0.25% to about 10% by weight of the final end-use hair-care composition. Other components which may be included in hair-care formulations include, for example, a solvent or diluent such as water and/or alcohol, surfactants, thickeners, coloring agents, preservatives, additional conditioning agents and humectants, among numerous others.

In the case of shave creams and gels, after-shave lotions and shave-conditioning compositions (for example, pre-electric shave formulations), the compositions according to the present invention are included in amounts ranging from about 0.25% to about 15% or more by weight, more preferably about 0.5% to about 10% by weight. Other components which may be included in these end-use compositions include, for example, water, and at least one or more of emollients, humectants and emulsifiers and optionally, other conditioning agents, medicaments, fragrances and preservatives.

In the case of skin lotions and creams, the present compositions are included in amounts ranging from about 0.25% to about 25% by weight, more preferably, about 0.5 to about 10% by weight. Additional components which may be employed in these compositions include, for example, water, emollients and emulsifers and optionally, other conditionoing agents medicaments, fragrances and preservatives.

In the case of sunscreens and skin-protective compositions, the present compositions are included in amounts ranging from about 0.25% to about 20% or more by weight, preferablyt about 0.5% to about 7.5% by weight of the final formulations. Additional components which may be employed in these compositions may include, for example, a UV absorbing composition such as para-amino benzoic acid (PABA) or a related UV absorber or a pigment such as $TiO_2$, water or oil, and optional components including, for example, one or more of an oil, water, suspending agents, other conditioning agents and emollients, among others.

In the case of bar and liquid soaps and hard surface and carpet cleaners, compositions according to the present invention are included in amounts ranging from about 0.25% to about 20% by weight or more, preferably about 0.5% to about 10% by weight. Additional components which may be included in bar and liquid soaps include water and surfactants and optionally, bacteriacides, fragrances and colorants, among others.

In preparing compositions according to the present invention, the tertiary amine is first prepared (in preferred embodiments, through transamidification of a triglyceride such as vegetable oil or cocoanut oil with, for example, aminopropyldimethyl amine using standard preparations available in the art) and is subsequently reacted with a quaternizing agent, as described in detail hereinabove. Generally, the tertiary amine is reacted with from about 1% to about 99% (on a mole-to-mole basis) of a quaternizing agent to produce a quaternary ammonium salt of the tertiary amine. The remaining unquaternized tertiary amine may thereafter be acidified with a carboxylic acid to produce a composition which comprises between about 1% and 99% by weight of a quaternized tertiary amine and about 99% to about 1% by weight of an acidified (preferably a pure di- or polycarboxylic acid, and no more than about 20%, preferably, no more than about 10% by weight of the carboxylic acid of a monocarboxylic acid) tertiary amine carboxylate, the quaternized tertiary amine and tertiary amine carboxylate being preferably derived from the same tertiary amine. In certain preferred embodiments, the tertiary amine contains more than one amine, in which case a molecule may contain a quaternary group on one or more positions of the molecule and a carboxylate salt on another or more positions of the molecule. In preferred embodiments according to the present invention, the carboxylic acid used to neutralize unreacted tertiary amine is a di- or poly carboxylic acid, such that a single carboxylic acid-containing molecule may produce a carboxylate salt at more than one position of the carboxylic acid compound. Depending upon the tertiary amine compound chosen and the carboxylic acid chosen, the resulting molecule may be extremely large and polymeric in character. In certain embodiments, rather than reacting the individual chemical reactants seriatim, it may be possible to add one or more of the starting amines after a particular reaction occurs (for example, quaternization), i.e., before introducing the carboxylic acid for neutralization.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Materials and Methods

In performing the following syntheses and preparing the following final formulations, the reagents which are used are indicated in the specific examples. Solvents, where used, are preferably distilled prior to use. Sources of other materials are indicated in the appropriate experimental section. In most instances, although not in every instance, trademarked materials are available from Alzo, Inc., Sayreville, N.J.

Examples

Example 1 represents an exemplary synthesis of compositions according to the present invention. Examples 2 and 3 may be made by analogy following the method set forth for the product of Example 1.

Example 1

Synthesis of Dimeramidopropyl Ethyldimonium Ethosulfate Dimer Dilinoleate (DAS-D)

STEP #1—Synthesis of Bis-propyl methyl amine dimer (FOAMINE D)

1. Using Dilinoleic Acid (DIMER ACID from Emery Henkel Cincinnati, Ohio, Unichema, Chicago, Ill.) 564 (1 MOL. OR EQ.) and Dimethylamino propyl amine (DMAPA) 260 (2.55 MOLS.)

Into 2 liter round-bottomed flask equipped with condenser and stirrer, charge Dimer Acid (1 Mol.) with $N_2$ on heat to 50–60° C.
2. Slowly add the DMPA; this is an exothermic reaction (neutralization reaction).
3. When all amine is in, raise the temperature slowly to 120° C.; hold for 1 hour. Raise to 140° C., hold for 1 hour. Raise to 160° C., reflux for 2 hours.
4. Cool to 80° C. Apply partial vac to strip excess amine and water when vac is full (29"). Raise temperature to 150–155° C.
5. When all excess amine is out, cool to 80° C.—release vacuum.
6. Check acid #—if higher than 3.0, repeat above steps by adding 0.5 Mol. (more) DMPA. When batch is finished, move to Step #2.

STEP #2—Synthesis of Dimer Acid Bis (Amidopropyl-N,N-Dimethyl-N-Ethyl Ammonium Ethyl Sulfate) (FOAMQUAT DAS)

FOAMINE D prepared as per Step #1, above 732 (1 Mol.=2 Eq.)
Diethylsulfate (DES) 154(1 Mol.)
Propylene glycol (POLY GLYCOL) 120 (1.58 Diluent)

PROCEDURE:

1. To Foamine D, add Poly Glycol with $N_2$ cover.
2. Heat to 75–80° C. Turn heat off.
3. Slowly drop in DES (this is an exothermic reaction).
4. When all DES is in, hold batch at 75–80° C. for 1 hour.
5. Check %, free amine should be about 40%.

STEP #3—Synthesis of Final Product Dimeramidopropyl Ethyldimonium Ethosulfate Dimer Dilinoleate* (NEQUAT DAS-D)

FOAMQUAT DAS 1006 (prepared in Step #2, above) (1 Mol.)
DIMER ACID 284 (0.5 Mol.=1 Eq.)

PROCEDURE:

1. Heat DAS to 60–65° C.
2. With $N_2$, slowly add Dimer Acid. Mix until uniform.
3. Test acid and alkali value—if within acceptable limits, unload batch.

*Note—Chemical name of DAS-D also known as Bis [Dimer Dilinoleate-Bis-(Amidopropyl-N,N-Dimethyl Ammonium Ethyl Sulfate)] Dimer Dilinoleate Quat/Ammonium Salt

Examples 2 and 3

[Dimer Dilinoleate-Bis-(Amidopropyl-N,N-Dimethy)1 Ammonium Ethyl Sulfate) Dimer Dilinoleate Quat/Ammonium Salt (DL-D) and [Dimer Dilinoleate-Bis-(Amidopropyl-N,N-Dimethy)1 Ammonium Ethyl Sulfate/Soyamidopropyl-N,N-Dimethyl]Dimer Dilinoleate Quat/Ammonium Salt (SO-D)

Figure 1:
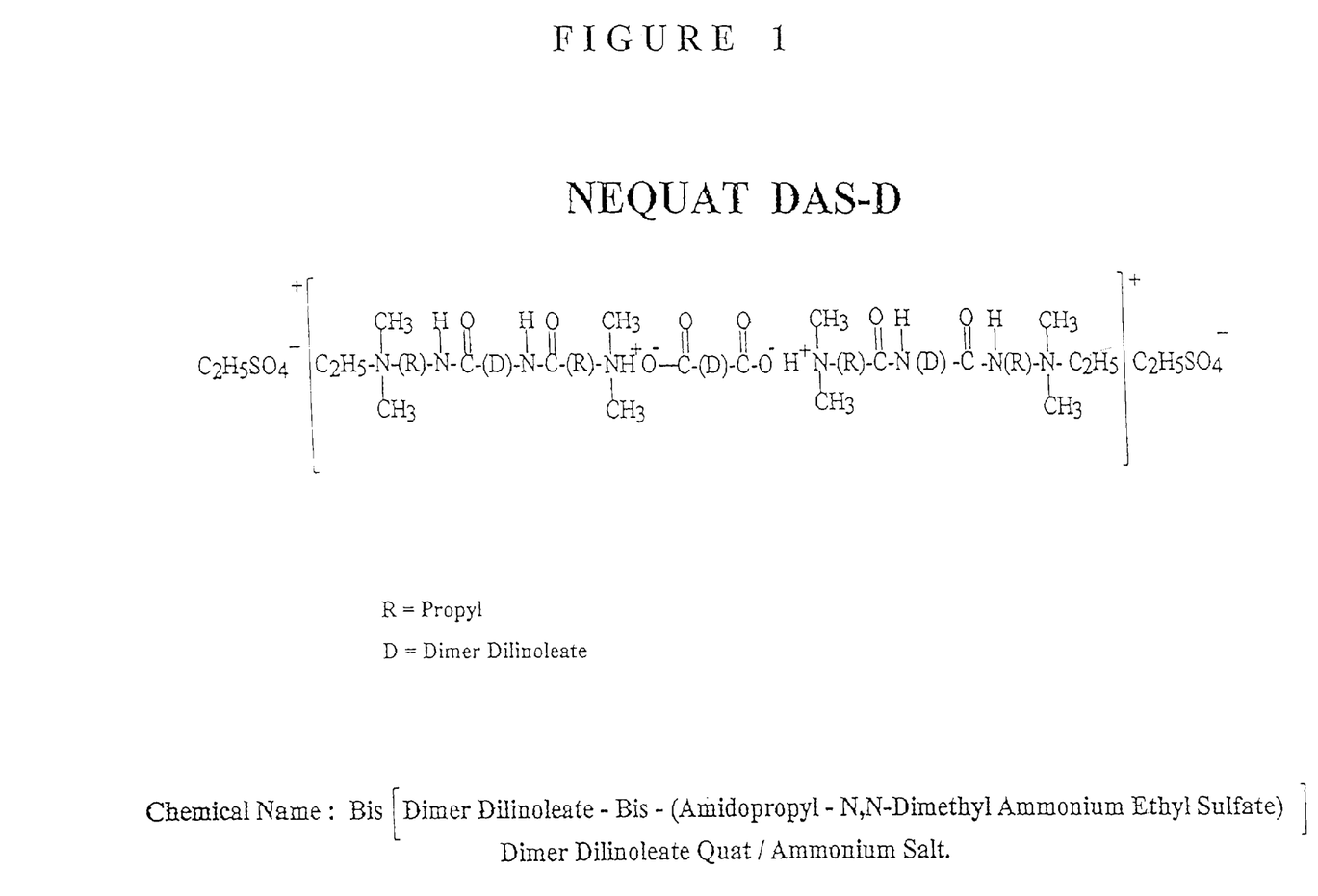
Figure 2:
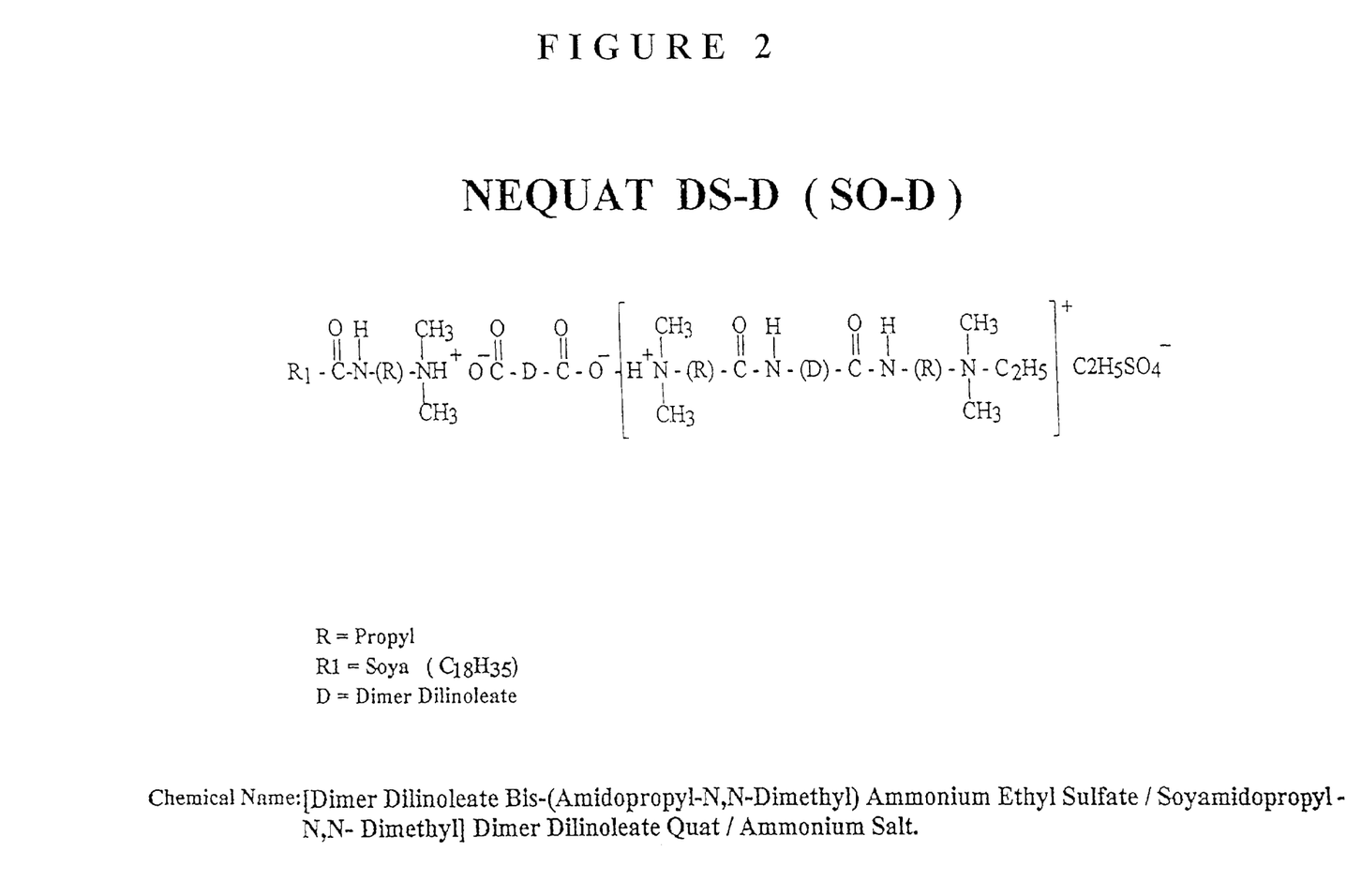
Figure 3:
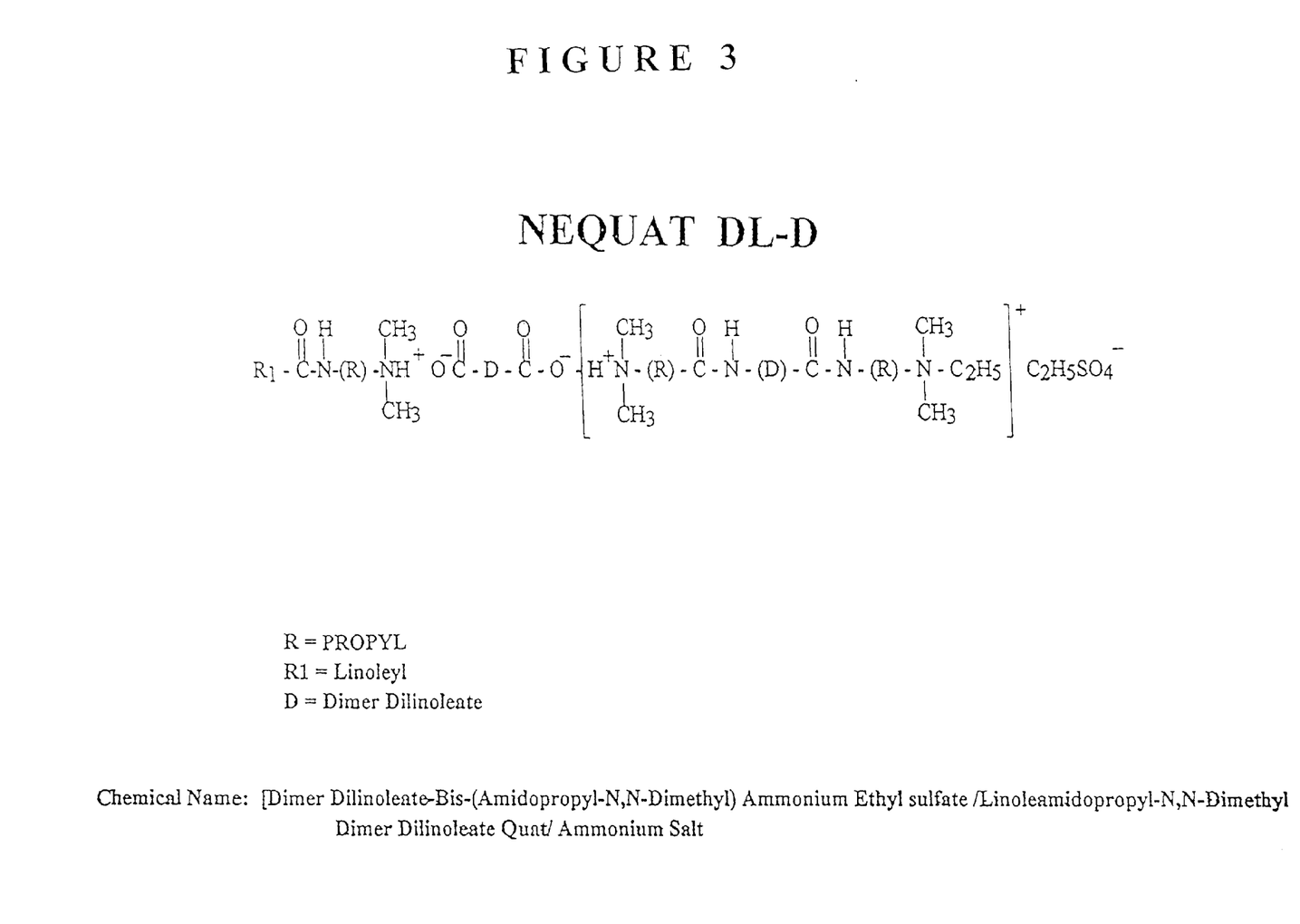

Using the general procedure established for example 1, two additional products according to the present invention are synthesized. These are [Dimer Dilinoleate-Bis-(Amidopropyl-N,N-Dimethy)1 Ammonium Ethyl Sulfate) Dimer Dilinoleate Quat/Ammonium Salt (Nequat DL-D) and [Dimer Dilinoleate-Bis-(Amidopropyl-N,N-Dimethyl 1 Ammonium Ethyl Sulfate/Soyamidopropyl-N,N-Dimethyl] Dimer Dilinoleate Quat/Ammonium Salt (SO-D) which are synthesized by analogy using the synthesis for DAS-D of Example 1. In the case of DL-D, instead of reacting all dimer acid with Foamquat as indicated, Foamquat is reacted with dimer acid in the third step (non-stoichiometric such that free carboxylic acid moieties remain in the dimer acid) and these remaining acid moieties are reacted with linoleamidopropyl dimethyl amine (which can be synthesized by standard methods readily available in the art or purchased as Foamine LO-80, available from Alzo, Inc.) in a fourth step to produce the final DL-D. In the case of SO-D, the reactions are the same as for DL-D, except that soyamidopropyl dimethyl amine (prepared analogously to linoleamidopropyl dimethyl amine from soy oil instead of linoleic acid or purchased as Foamine SO from Alzo, Inc., Sayreville, N.J.) is used instead of Foamine LO-80 in the final step to produce SO-D. Otherwise, the syntheses are virtually identical. The chemical formulas for DAS-D, DS-D and DL-D appear in attached FIGS. 1, 2 and 3.

Example 4

| | MOISTURIZING SUNSCREEN | |
|---|---|---|
| A. | Water (Deionized) | 73.45% |
| | Preservative | 0.05 |
| B. | NECON LO-80 (Linoleamidopropyl dimethylamine dimer Dilinoleate) | 1.5 |
| | NEQUAT (DLD-60/40)* | 3.5 |
| | Octylmethoxy Cinnmate | 7.5 |
| | Glyceryl Tricaprylate/Caprate | 5.0 |
| | Benzophenone-3 | 3.0 |
| | Emulsifying Wax | 2.0 |
| | Behenyldimethylamidopropyl Amine Behenate | 1.0 |
| C. | Polyacrylamide and Laureth 7 | 2.0 |
| D. | Isohexyl Decanoate | 1.0 |
| | PROCEDURE: | |
| | Combine A and heat to uniformity at 60° C. | |
| | Combine B; heat to 55° C. | |
| | Add C to A slowly with good agitation. | |
| | Combine AC and B with agitation. | |
| | Add D with agitation to the total. | |

*Indicates the ratio of quaternization to tertiary amine salt formation.

Example 5

| | CATIONIC TEXTURIZING SHAMPOO | |
|---|---|---|
| A. | Water (Deionized) | 53.0% |
| | TEA Lauryl Sulfate | 20.0 |
| | Sodium Laureth Sulfate | 10.0 |
| | Cocoamidopropyl Betaine, 40% | 8.0 |
| | Preservative | 0.5 |
| B. | Acetamide MEA | 4.0 |
| | NEQUAT (DLD-80/20)* | 2.0 |
| | Linoleylamidopropyldimethylamine Dilinoleate | 1.0 |
| | Octyldodecyl Erucate | 0.95 |
| | PROCEDURE: | |
| | Combine A with agitation and heat to uniformity at 65 ° C. | |
| | Heat Part B to 65 ° C. with agitation. Blend into Part A. | |

*Indicates the ratio quaternization to to tertiary amine salt formation.

Example 6

CATIONIC MOISTURIZING BODY WASH

| | INGREDIENTS | %, WEIGHT |
|---|---|---|
| A. | Water (Deionized) | 61.5 |
| | Preservative | 0.5 |
| B. | NEQUAT (DLD-60/40) | 1.0 |
| C. | Sodium Cocoyl Isethionate | 3.0 |
| D. | Sodium Laureth Sulfate | 3.0 |
| | Octyldodecyl Erucate | 1.0 |
| B. | Cocamidopropyl Betaine | 30.0 |
| | Mica (and) Titanium Dioxide | 0.2 |

PROCEDURE:

1. Combine A. Dissolve B in A while agitating. Heat to 70° C.
2. Add C while agitating. Heat to 80° C.
3. Combine D; add to ABC while agitating.
4. Add E while agitating.

Example 7

CATIONIC MOISTURIZING HAND CREAM

| | INGREDIENTS | %, WEIGHT |
|---|---|---|
| A. | Water (Deionized) | 90.5 |
| | Preservative | 0.05 |
| B. | Emulsifying Wax | 1.0 |
| | Behenyldimethylamidopropyl Behenate | 2.0 |
| | Octyldodecyl-12-Hydroxystearate-Dilinoleate | 3.0 |
| C. | NEQUAT (DLD-80/20) | 2.0 |
| D. | Isohexyl Decanoate | 1.45 |

PROCEDURE:

1. Combine A and heat to uniformity at 50° C.
2. Combine B; heat to 50° C. or until material is homogeneous.
3. With agitation, combine A and B.
4. Add C to AB with agitation and heat.
5. Add D with heat and agitation to ABC.

Example 8

AFTER SHAVE LOTION

| INGREDIENTS | %, WEIGHT |
|---|---|
| NEQUAT DLD-80/20 | 1.5 |
| ETHANOL SD-40, Anhy. | 73.5 |
| Laureth-2-Benzoate | 3.0 |
| Deionized Water | 22.0 |
| | 100.0 |

The inclusion of NEQUAT into the formulation for after shave lotion, provides a refreshing, cooling feeling on the skin that leaves it soft for hours.

Example 8

CATIONIC SOOTHING BODY LOTION

| | INGREDIENTS | %, WEIGHT |
|---|---|---|
| A. | Dermol 20-SD | 1.4 |
| | Bis(Octyldodecyl Stearoyl) Dimer Dilioleate) | |
| | Dermol M-5 Octanoic/Decanoic Acid Triglyceride | 12.0 |
| | Dermol M20-Isoeicosanyl 12-Hydroxystearate | 2.1 |
| | Dermol OE Oleyl Erucate | 2.0 |
| B. | Water q.s. to | 100.0 |
| | Preservative | q.s. |
| | Foamid AME-100 (Acetic acid monoethanolamine) | 5.00 |
| | Xanthum Gum | 0.30 |
| | Hectorite (and) Hydroxyethylcellulose | 0.50 |
| C. | Soy Bean Protein (Hydrolyzed) (Vegesyl HGP 8572) | 5.0 |
| | Nequat DLD-80/20 | 5.0 |

PROCEDURE:

1. Prepare separately A and B at 80° C.
2. Add A to B at 80° C., with strong stirring.
3. Cool to 50° C. and with stirring, add C.
4. Cool to room temperature.

Example 8

CATIONIC WATER IN OIL CREAM

| | INGREDIENTS | %, WEIGHT |
|---|---|---|
| A. | Polyderm PPI-PE (Alzo, Inc.) | 10.00 |
| | Dermol M-20 | 10.00 |
| | Dermol OE (oleyl eruacate) | 2.00 |
| | Dermol DGDIS (diglycerol diisostearate) | 5.00 |
| | Wickenol 139 | 2.00 |
| | Waxenol 801 | 1.50 |
| | BHT (and) Glyceryl Stearate (and) Glyceryl Oleate (and) Ascorbyl Palmitate (and) Citric Acid (and) Propylene Glycol, (Oxynex 2004, Rona Merck). | .02 |
| | Nequat DLD-80/120 | 0.50 |
| B. | Magnesium Sulfate | 2.00 |
| | Methyl Paraben | 0.15 |
| | Propyl Paraben | 0.05 |
| | Phenoxyethanol | 0.50 |
| | Deionized Water to | 100.00 |

PROCEDURE:

1. Heat A to 80° C.
2. Heat B to 70–80° C. and emulsify into A.
3. Mix and cool to desired fill temperature.

Example 9

CATIONIC MOISTURIZING LOTION (OIL FREE)

| | INGREDIENTS | %, WEIGHT |
|---|---|---|
| A. | Dermol Joba (Cetearyl octanoate) | 5.00 |
| | Glyceryl Stearate (and) PEG-100 | 1.25 |
| | Triple Pressed Stearic Acid | 1.25 |
| | Cetearyl Alcohol (and) Ceteareth-20 | 1.25 |
| | Dermol IHD (Isohexyl Decanoate) | 1.25 |
| | PEG-100 Stearate | 0.5 |

CATIONIC MOISTURIZING LOTION (OIL FREE)

| | INGREDIENTS | %, WEIGHT |
|---|---|---|
| | Nequat DLD-80/20 | 0.5 |
| B. | Deionized Water | q.s. |
| | Carbomer 980 | 0.20 |
| C. | Foamid AME-100 | 3.00 |
| D. | Triethanolamine, 99% | 0.2 |
| E. | Water | 1.50 |
| | Butylene Glycol | 1.50 |
| | Locust Bean Gum | 3.00 |

PROCEDURE:

1. Heat and combine A to 80° C.
2. In a separate vessel, combine B and heat to 80° C.
3. Add C to B.
4. Add A.
5. At 55° C., add D.
6. At 35° C., add E. Mix until temperature of 25° C. is reached.

Example 10

2 IN 1 SHAMPOO

| | INGREDIENTS | % WEIGHT |
|---|---|---|
| A. | Water | 63.99% |
| | Tetra sodium EDTA | 0.01% |
| B. | Polyderm PPI-SA (PEG-2 Soyamine Polymer with Isophorone Diiisocyanate- Alzo, Inc.) | 1.00 |
| | Polysorbate 80 | 1.00 |
| | Foamid AME | 3.00 |
| | Sodium Lauryl Sulfate | 25.00 |
| | Foamtaine CAB (Cocamidopropyl Betaine) | 5.00 |
| | Nequat (Examples 1–3) | 1–5% |
| | Macpearl 15-DS (Ethylene Glycol Distearate, 35%) | 1.00 |
| C. | Paragon II (DMDM Hydantoin, Methyl Paraben Propyl Paraben and Propylene Glycol) | 2.00 |
| | Sodium Chloride (to desired Viscosity) | q.s |
| | Citric Acid (to adjust pH) | q.s. |

PROCEDURE:

1. In a clean and sanitized vessel add all of Phase B and add gentle heat Until dispersed (100° F. Maximum)
2. Add the Ingredients of Phase C to Phase B with slow agitation.
3. When uniform, add Phase A and mix until dispersed.
4. Adjust the pH, then adjust the viscosity.

Example 11

Aerosol Shaving Cream

| | INGREDIENTS | % WEIGHT |
|---|---|---|
| A. | Dimethicone Copolyol | 2.50 |
| | Polyderm PPI-Si (50% in glycerine) | 0.75 |
| | Dimethiconol Polymer with 3-Isocyanatomethyl-3,5,5-Trimethylcyclohexyl Isocyanate (Alzo, Inc.) | |
| | Stearic Acid | 4.00 |
| | Myristic Acid | 3.00 |

Aerosol Shaving Cream

| | INGREDIENTS | % WEIGHT |
|---|---|---|
| | Lanolin | 0.50 |
| | Monoderm I-82-(Ethyl Hexanol Dimer with Isophorone Diisocyanate Alzo, Inc.) | 1.00 |
| | Nequat DAS-D | 2.00 |
| B. | Sorbitol (70%) | 5.00% |
| | Triethanolamine | 3.50% |
| | Water | q.s. to 100% |
| C. | Menthol | 0.10% |
| | Fragrance | q.s. |
| | Preservative | q.s. |

Ratio of propellant to formula = 9:1.

PROCEDURE:

1. Mix and Heat phases A to 176° F. and B to 176° F.
2. Add Phase A to Phase B with good agitation. Hold temperature for 15 minutes to saponify.
3. Mix Phase C to a temperature of 86° F. Add Phase C Just prior To packaging.

Example 12

Nequat Solubility

Nequat DL-D was tested for its solubility in a number of solvents. Essentially 2% by weight of Nequat was added to the following solvents at room temperature.

| | 2.0% | | |
|---|---|---|---|
| | DL-D 80-20 I# 118-141 | DL-D 60-80 I# 118-147 | DL-D-20-80 I# 118-151 |
| GLYCEROL | S | S | D |
| POLY GLYCOL | S | S | S |
| WATER | S | D | I |
| MINERAL OIL | PD | PD | PD |
| VEGETABLE OIL | I | I | D |
| SILICONE | I | I | I |
| IPM | PD | P | P |
| FOAMID C | S | S | S |
| FOAMTAINE CAB | S | S | S |

LEGEND:
S - SOLUBLE
I - INSOLUBLE
I - DISPERSIBLE
PD - PARTIALLY DISPERSIBLE

Example 13

Shave Formulation

When the present invention was incorporated into a shave formulation and compared to commercially available products, it was reported that 24 of 25 participants in the study preferred the shave cream product which incorporated the present invention in contrast to the commercially available product. The participants preferred the shave cream formulations of the present invention for the following qualities:

closeness of shave;

less damage;

softer skin feel;

longer lasting fragrance;

smoother shave;

ease of shave.

Example 14

Conditioning Shampoos and Hair Conditioners

It was unexpectedly discovered that when the present invention was introduced into 2:1 conditioning shampoos and into hair conditioners, the product was preferred over commercially available products. Results from a panel of 35 individuals indicate that the present invention provided excellent conditioning of damaged hair and performed better than commercially available products. Approximately 90% of the panelists chose the present compositions over commercially available products. The present invention provided the following superior qualities in final formulations:

better feel of hair after use;

better appearance of hair after use;

increased viscosities of formulations making them more usable.

The present formulations also performed better than the commercial formulations during manufacturing that the manufacturer is able to reduce the maximum temperature of the phases, thereby reducing manufacturing time and consequently, costs of maufacture.

It is to be understood by those skilled in the art that the foregoing description and examples are merely illustrative of the present invention, and should in no way be intrepreted as limiting the scope of the present invention. Variations of the detail presented herein may be made without departing from the spirit and scope of the present invention as defined by the following claims.

What is claimed is:

1. A chemical composition comprising the neutralization product of at least one amine neutralization compound and a carboxylic acid, said amine neutralization compound comprising about 1% to about 100% by weight of the total amount of said amine neutralization compound of a first amine compound and 0% to about 99% by weight of a second amine compound, said first amine compound comprising a polyamine containing at least one tertiary amine group and at least one quaternary amine group, said tertiary amine group of said first amine compound reacting with said carboxylic acid to produce a tertiary ammonium carboxylate salt, said second amine compound containing at least one primary, secondary or tertiary amine group reacting with said carboxylic acid to produce an ammonium carboxylate salt with the proviso that when said second amine contains only primary and/or secondary amine groups, the amount of said second amine in said amine neutralization compound is no greater than about 20% by weight of said first and second amine and said carboxylic acid comprises at least about 80% by weight of a polycarboxylic acid.

2. The composition according to claim 1 wherein said carboxylic acid comprises about 100% by weight polycarboxylic acid.

3. The composition according to claim 2 wherein said polycarboxylic acid is a dicarboxylic acid.

4. The composition according to claim 1 wherein said first amine compound is a diamine.

5. The composition according to claim 1 wherein said first amine compound has the structure:

$$\begin{array}{c} R_1 \\ \diagdown \\ R_2 \end{array} N-R''-N\overset{H}{\underset{}{|}}-\overset{O}{\underset{}{\|}}C-R'-\overset{O}{\underset{}{\|}}C-\overset{H}{\underset{}{|}}N-R''-\overset{+}{N}\overset{R_1}{\underset{R_2}{\diagup}}R_3 \quad T^-$$

where R' is a $C_6$ through $C_{36}$ linear or branch-chained saturated or unsaturated alkyl group which is substituted or unsubstituted, monomeric or dimeric, a phenyl or benzyl group or substituted phenyl or benzyl group, an alkylphenyl, alkylbenzyl or substituted alkylphenyl or alkylbenzyl group; and R'', $R_1$ and $R_2$ are each independently a $C_1$ through $C_{36}$ linear or branch-chained saturated or unsaturated alkyl group which is substituted or unsubstituted, monomeric or dimeric, a phenyl or benzyl group or substituted phenyl or benzyl group, an alkylphenyl, alkylbenzyl or substituted alkylphenyl or alkylbenzyl group, or poly(alkylene oxide) ranging in size from about 2 to about 150 alkylene oxide units and $R_3$ is any group compatible with the formation of a quaternary amine group and $T^-$ is a counterion of the quaternary group.

6. The composition according to claim 5 wherein $R_1$ and $R_2$ are $C_1$ through $C_{15}$ linear or branch-chained alkyl groups.

7. The composition according to claim 5 wherein $R_1$ and $R_2$ are the same or different and are methyl, ethyl, propyl or isopropyl groups.

8. The composition according to claim 5 wherein $R_3$ is a methyl, ethyl or benzyl group.

9. The composition according to claim 1 wherein said second amine compound is a diamine.

10. The composition according to claim 5 wherein said second amine has the structure:

$$\begin{array}{c} R_1 \\ \diagdown \\ R_2 \end{array} N-R''-N\overset{H}{\underset{}{|}}-\overset{O}{\underset{}{\|}}C-R'-\overset{O}{\underset{}{\|}}C-\overset{H}{\underset{}{|}}N-R''-N\overset{R_1}{\underset{R_2}{\diagup}}$$

where R' is a $C_6$ through $C_{36}$ linear or branch-chained saturated or unsaturated alkyl group which is substituted or unsubstituted, monomeric or dimeric, a phenyl or benzyl group or substituted phenyl or benzyl group, an alkylphenyl, alkylbenzyl or substituted alkylphenyl or alkylbenzyl group; and R'', $R_1$ and $R_2$ are each independently a $C_1$ through $C_{36}$ linear or branch-chained saturated or unsaturated alkyl group which is substituted or unsubstituted, monomeric or dimeric, a phenyl or benzyl group or substituted phenyl or benzyl group, an alkylphenyl, alkylbenzyl or substituted alkylphenyl or alkylbenzyl group, or poly(alkylene oxide) ranging in size from about 2 to about 150 alkylene oxide units.

11. The composition according to claim 10 wherein $R_1$ and $R_2$ are $C_1$ through $C_{15}$ linear or branch-chained alkyl groups.

12. The composition according to claim 10 wherein $R_1$ and $R_2$ are the same or different and are methyl, ethyl, propyl or isopropyl groups.

13. The composition according to claim 1 wherein said second amine compound is a tertiary amine.

14. The composition according to claim 1 wherein said second amine compound is a di-tertiary amine.

15. The composition according to claim 1 wherein said first amine compound is dilinoleamidopropyl dimethylamine quaternized with a methyl, ethyl or benzyl group.

16. The composition according to claim 5 wherein said second amine compound is selected from the group consisting of linoleamidopropyl dimethylamine and dilinoleamidopropyl dimethylamine.

17. The composition according to claim 1 wherein said second amine compound is a fatty amido tertiary amine.

18. The composition according to claim 1 wherein said carboxylic acid is a polycarboxylic acid and said amine neutralization compound and said polycarboxylic acid are included in said composition in a molar ratio from about 1:10 to about 10:1.

19. The composition according to claim 1 wherein said carboxylic acid is a polycarboxylic acid and said amine neutralization compound and said polycarboxylic acid are included in said composition in a molar ration from about 1:3 to about 3:1.

20. The composition according to claim 1 wherein said carboxylic acid is a polycarboxylic acid and said amine neutralization compound and said polycarboxylic acid are included in said composition in a molar ratio of about 1:1.

21. The composition according to claim 5 wherein $T^-$ is selected from the group consisting of chloride, bromide, iodide, sulfate, alkyl sulfate and phosphate.

22. The composition according to claim 21 wherein $T^-$ is chloride or ethyl sulfate.

23. The composition according to claim 5 wherein said second amine has the structure:

where R' is a $C_6$ through $C_{36}$ linear or branch-chained saturated or unsaturated alkyl group which is substituted or unsubstituted, monomeric or dimeric, a phenyl or benzyl group or substituted phenyl or benzyl group, an alkylphenyl, alkylbenzyl or substituted alkylphenyl or alkylbenzyl group; and R", $R_1$ and $R_2$ are each independently $C_1$ through $C_{36}$ linear or branch-chained saturated or unsaturated alkyl group which is substituted or unsubstituted, monomeric or dimeric, a phenyl or benzyl group or substituted phenyl or benzyl group, an alkylphenyl, alkylbenzyl or substituted allylphenyl or alkylbenzyl group, or poly(alkylene oxide) ranging in size from about 2 to about 150 alkylene oxide units.

24. The composition according to claim 23 wherein $R_3$ is a methyl, ethyl or benzyl group.

25. The composition according to claim 11 wherein $R_3$ is a methyl, ethyl or benzyl group.

26. The composition according to claim 12 wherein $R_3$ is a methyl, ethyl or benzyl group.

27. The composition according to claim 5 wherein said second amine compound is selected from the group consisting of linoleamidopropyl dimethylamine and dilinolcamidopropyl dimethylamine and wherein $R_3$ is a methyl, ethyl or benzyl group.

28. The composition according to claim 5 wherein said second amine compound is a fatty amido tertiary amine and wherein $R_3$ is a methyl, ethyl or benzyl group.

29. The composition according to claim 23 wherein said carboxylic acid is a polycarboxylic acid, said amine neutralization compound and said polycarboxylic acid are included in said composition in a molar ratio from about 1:10 to about 10:1 and $R_3$ is a methyl, ethyl or benzyl group.

30. The composition according to claim 23 wherein said carboxylic acid is a polycarboxylic acid, said amine neutralization compound and said polycarboxylic acid are included in said composition in a molar ratio from about 1:3 to about 3:1 and $R_3$ is a methyl, ethyl or benzyl group.

31. The composition according to claim 23 wherein said carboxylic acid is a polycarboxylic acid, said amine neutralization compound and said polycarboxylic acid are included in said composition in a molar ratio of about 1:1 and $R_3$ is a methyl, ethyl or benzyl group.

32. The composition according to claim 29 wherein $R_3$ is a methyl or ethyl group.

33. The composition according to claim 30 wherein $R_3$ is a methyl or ethyl group.

34. The composition according to claim 21 wherein $R_3$ is a methyl, ethyl or benzyl group.

35. The composition according to claim 22 wherein $R_3$ is a methyl, ethyl or benzyl group.

36. The composition according to claim 5 wherein $T^{31}$ is chloride or ethyl sulfate.

37. The composition according to claim 8 wherein $T^-$ is chloride or ethyl sulfate.

38. The composition according to claim 9 wherein $T^-$ is chloride or ethyl sulfate.

39. The composition according to claim 10 wherein $T^-$ is chloride or ethyl sulfate.

* * * * *